United States Patent [19]
Mitra et al.

[11] Patent Number: 6,056,975
[45] Date of Patent: May 2, 2000

[54] STABILIZED THYROID HORMONE PREPARATIONS AND METHODS OF MAKING SAME

[75] Inventors: Amit K. Mitra, Silver Spring, Md.; Raghunath Srinivas, Barrington, Ill.; Charles L. Thomas, III, Keithsville, La.

[73] Assignee: BASF Corporation, Mount Olive, N.J.

[21] Appl. No.: 09/156,844

[22] Filed: Sep. 18, 1998

Related U.S. Application Data

[63] Continuation of application No. 08/748,869, Nov. 14, 1996, Pat. No. 5,955,105
[60] Provisional application No. 60/006,738, Nov. 14, 1995, and provisional application No. 60/017,314, May 13, 1996.

[51] Int. Cl.[7] .................. A61K 9/20; A61K 9/36
[52] U.S. Cl. ............ 424/464; 424/465; 424/479; 424/480
[58] Field of Search .................. 424/464, 465, 424/479, 480

[56] References Cited

U.S. PATENT DOCUMENTS

| | | | |
|---|---|---|---|
| 4,369,172 | 1/1983 | Schor et al. | 424/419 |
| 4,666,703 | 5/1987 | Kopf | 424/470 |
| 4,851,228 | 7/1989 | Zentner et al. | 424/456 |
| 4,871,548 | 10/1989 | Edgren et al. | 424/488 |
| 5,102,666 | 4/1992 | Acharya | 424/487 |
| 5,225,204 | 7/1993 | Chen et al. | 424/484 |
| 5,275,820 | 1/1994 | Chang | 424/426 |
| 5,324,522 | 6/1994 | Krenning et al. | 424/456 |

FOREIGN PATENT DOCUMENTS

| | | |
|---|---|---|
| 0 550 108 A1 | 12/1992 | European Pat. Off. . |
| 42 18 577 A1 | 12/1994 | Germany . |
| WO 95/20953 | 8/1995 | WIPO . |
| WO 95/20954 | 8/1995 | WIPO . |
| WO 97/19703 | 6/1997 | WIPO . |

OTHER PUBLICATIONS

International Search Report—PCT/IB 96/01330, Apr. 16, 1997.

*Primary Examiner*—Thurman K. Page
*Assistant Examiner*—S. Howard
*Attorney, Agent, or Firm*—George A. Gilbert

[57] ABSTRACT

Disclosed are thyroid hormone preparations useful in pharmaceutical applications. These preparations are disclosed to contain thyroxine drugs in combination with an inorganic salt, a carbohydrate having a molecular weight of greater than 500, and glycine. The preparations are also disclosed to have a free water content less than 4.5% by weight of the preparation. Also provided are compositions containing a reduced carbohydrate, a water soluble polysaccharide, or galactose. The preparations have improved stability wherein they are provided as being stable to the extent that substantially no potency loss is measured when the preparation is stored at 40° C. and 75% relative humidity for 3 months.

38 Claims, No Drawings

STABILIZED THYROID HORMONE PREPARATIONS AND METHODS OF MAKING SAME

This application continued of U.S. application Ser. No. 08/748,869, filed on Nov. 14, 1996 now U.S. Pat. No. 5,955,105 and U.S. Provisional Applications Ser. No. 60/006,738, filed on Nov. 14, 1995, and Ser. No. 60/017,314, filed on May 13, 1996.

FIELD OF THE INVENTION

The present invention is directed to therapeutic agents for the treatment of hormone disorders, and is directed to stabilized pharmaceutical preparations containing thyroxine drugs, and especially levothyroxine sodium, which is the sodium salt of the levo isomer of thyroxine. Thyroxine is an active physiological thyroid hormone obtained from the thyroid gland of domesticated animals, or alternatively the hormone can be prepared synthetically. Levothyroxine and other thyroid hormones are known to serve as specific replacement therapy when the thyroid function has been reduced or is completely absent for a variety of disease states, including, for instance, myxedema, cretinism and obesity.

BACKGROUND OF THE INVENTION

Levothyroxine sodium is relatively stable in pure form, but pharmaceutical preparations containing levothyroxine hormone exhibit a relatively short shelf life, even when in solid unit dose form, and most particularly under conditions of high humidity and temperature.

U.S. Pat. No. 5,225,204 is directed to improving the stability of levothyroxine sodium. The patent claims stability is achieved in several embodiments. The first embodiment relates to mixing a commercial grade of levothyroxine sodium with polyvinyl pyrrolidone (PVP), at least partially dissolving the resulting mixture in a polar organic solvent, and adding a cellulose carrier compound. The solvent is removed by drying, to produce a resulting fine powder said to be a stable complex of levothyroxine sodium and polyvinyl pyrrolidone disbursed on the surface of the cellulose carrier component.

In a second embodiment of the '204 patent, the PVP is replaced by a Poloxamer.

In a third embodiment of the '204 patent, the levothyroxine sodium is at least partially dissolved in a polymer organic solvent in the absence of PVP and Poloxamer, and the cellulose carrier is added, after which the solvent is removed to leave the levothyroxine sodium adsorbed on the cellulose carrier.

A fourth embodiment of the '204 patent describes that stabilized levothyroxine sodium may be prepared in a dry state by mixing levothyroxine sodium with a cellulose complexing agent and subsequently combining this mixture with a cellulose carrier. Specifically, it is described in the '204 patent that levothyroxine sodium can also be effected by initially mixing it with a cellulose tableting agent using the geometric dilution technique and the same, or a second, cellulose tableting agent, such as microcrystalline cellulose, is added to the dry mixture. The tableting agent is described as a carrier or adsorbing agent. Other tableting aids such as hydroxypropyl cellulose, hydroxyethyl cellulose, sodium carboxymethyl cellulose, low substituted hydroxypropyl cellulose and hydroxypropylmethyl cellulose. These polymer cellulose compounds are known to be insoluble or partially soluble U.S. Pat. No. 5,225,204 indicates that most of the commonly used excipients may be mixed with the stabilized levothyroxine sodium, but certain carbohydrate excipients which are known as degrading agents of levothyroxine sodium should be avoided. These excipients include dextrose, starch, sugar and lactose.

Although U.S. Pat. No. 5,225,204 claims that the resulting pharmaceutical compositions are stable compositions, no stability data was presented. Examples 1 and 2 of the U.S. Pat. No. 5,225,204 were repeated (in repeating example 1 of U.S. Pat. No. 5,225,204, K-30 Plasdone was used instead of C-15 Plasdone, as C-15 Plasdone was not available. This difference is believed trivial, since the differences between the two products is only a molecular weight difference), and the resulting preparations were subjected to stability tests at ambient room temperature (ART) and at 30° C. and 40° C. with no humidity control. The resulting stability data are set forth below.

EXAMPLE 1 OF U.S. Pat. No. 5,225,204

| Condition | Interval | % Actual (S.D.) |
| --- | --- | --- |
| Initial | Initial | 100.0 |
| ART | 1 month | 92.3 ± (6.1) |
| ART | 2 months | 88.1 ± (2.7) |
| ART | 3 months | 87.2 ± (11.9) |
| 30° C. | 1 month | 86.1 ± (5.1) |
| 30° C. | 2 months | 95.3 ± (3.9) |
| 30° C. | 3 months | 87.8 ± (5.6) |
| 40° C. | 1 month | 95.0 ± (1.8) |
| 40° C. | 2 months | 94.7 ± (5.7) |
| 40° C. | 3 months | 91.9 ± (4.2) |

EXAMPLE 2 OF U.S. Pat. No. 5,225,204

| Condition | Interval | % Actual (S.D.) |
| --- | --- | --- |
| Initial | Initial | 97.0 ± (0.4) |
| ART | 1 month | 89.7 ± (2.3) |
| ART | 2 months | 68.3 ± (1.9) |
| ART | 3 months | 61.4 ± (1.9) |
| 30° C. | 1 month | 88.3 ± (1.6) |
| 30° C. | 2 months | 71.3 ± (1.3) |
| 30° C. | 3 months | 64.2 ± (0.1) |
| 40° C. | 1 month | 89.5 ± (0.6) |
| 40° C. | 2 months | 64.1 ± (0.1) |
| 40° C. | 3 months | 62.5 ± (1.2) |

Example 1 of U.S. Pat. No. 5,225,204 involved the use of PVP. A non-uniform granulation was obtained, which was difficult to convert into solid dosage form. Unknown peaks were visible in the stability samples, and the peaks are speculated to be due to an adduct formed in solution between levothyroxine sodium and PVP.

Example 2 of U.S. Pat. No. 5,225,204 was prepared using dry mixing of levothyroxine sodium with hydroxypropyl cellulose, with subsequent combination of this mixture with a microcrystalline cellulose carrier. The stability test results are substantially worse than commercial products which were commercially available at the time the application which matured into U.S. Pat. No. 5,225,204 was filed.

SUMMARY OF THE INVENTION

The present invention is directed to providing an improved, stable, solid dosage form of thyroid hormone pharmaceutical preparations. The preparations contain an effective amount of a thyroid drug, at least one excipient, such as a diluent or bulker, which excipient is an inorganic salt, a carbohydrate having a molecule weight of greater than 500, or glycine.

An embodiment of the present invention is directed to a stable solid dosage form of a thyroid hormone preparation containing a water soluble polysaccharide. A further embodiment of the invention contains a reduced carbohydrate (e.g. typical reduction of ketoses and aldehydes), preferably mannitol. Also contemplated by the present invention is a preparation containing galactose.

The preparation preferably has a free water content of less than 4.5% by weight and a pH greater than 7 (one gram of the preparation mixed with one milliliter of water). Such preparations are stable to the extent that when subjected to stability testing at 40° C. and 75% RH for 3 months, substantially no potency loss can be measured (e.g. the potency loss is less than about 10%). It is preferred that the stability of the preparations of the present invention, when tested at 40° C. and 75% RH for 1 month, be such as to result in a potency loss of less than about 3–5%.

DETAILED DESCRIPTION OF THE INVENTION

Levothyroxine sodium itself, in contrast to the same drug in solid dosage formulations, is stable at controlled room temperature for a prolonged period of time. It is believed that the stability of the drug when placed in solid dosage formulations is probably due to drug-excipient interaction. It has now been found that thyroid hormones and especially levothyroxine sodium are compatible with some excipients but incompatible with others. Carbohydrates, such as starch and maltodextrin, are compatible with thyroid hormones, whereas lactose, glucose and sucrose were determined to be incompatible. By the use of suitable compatible binders, glidents, lubricants and disintegrants, thyroid hormones can be formulated into tablet, capsule, or powder dosage forms. It is also possible to incorporate a small quantity of incompatible excipients (i.e., up to 10% by weight and preferably less than 5% by weight) in the formula without sacrificing product stability.

Preferred embodiments of the present invention are prepared in the substantial absence of lactose, glucose, sucrose, polyvinylpyrrolidone, andlor a Poloxamer. According to the present invention, a direct compression tablet dosage form with good content uniformity of thyroid hormone drugs, such as levothyroxine sodium, can be obtained. It is possible to develop a stable, direct compression formula for levothyroxine sodium, and also possible to develop a stable, wet granulation formula for levothyroxine sodium.

When the excipient is a bulker or diluent comprising a carbohydrate having a molecular weight greater than 500, it is preferred that the solid dosage form comprises a soluble polysaccharide having a dextrose value of less than 25, preferably less than 10. Preferred polysaccharides include maltodextrin, β cyclodextrin, and hydroxypropyl-β-cyclodextrin. The most preferred polysaccharides are those that impart a dissolution profile such as for those outlined below for compositions containing maltodextrin and levothyroxine having a small particle size.

It is possible to change the dissolution rate of the product, and thus the rate of delivery of the drug in vivo, by changing the composition of the formula, and especially by varying the proportion of the disintegrant(s). Also, the rate of dissolution of the drug can be varied by changing the hardness of the tablet dosage form, suitably by changing the amount of compression applied to the tablet dosage form during tableting operations.

As is known in the art, a capsule dosage form usually contains filler, disintegrant, glidents and lubricant, along with the active ingredient, and a tablet dosage form usually contains the same components, together with a binder. Proper selection of each of these components produces a stable formula for levothyroxine sodium or other thyroid preparations in solid dosage form. Flavorants and colorants are conventionally added as desired.

Thyroid hormones, and especially levothyroxine sodium, are stable in connection with binders that are (a) carbohydrates having a molecular weight of greater than 500, preferably less than 1,500,000 and more preferably between 500 and 160,000, (b) inorganic salts, and (c) glycine. Suitable carbohydrate binders include microcrystalline cellulose, maltodextrin, starch and hydroxypropyl cellulose having a molecular weight between 80,000 and 1,150,000. It is surprising that soluble glucose polymers, such as maltodextrins, preferably a soluble glucose polymer having a molecular weight of 500 to 3600, when used in combination with the insoluble or partially soluble cellulose polymers, result in a solid dosage composition that has improved and superior, stability, content uniformity, good tableting and dissolution properties.

Fillers which can be used in the present invention include the microcrystalline cellulose and starch mentioned above, as well as alkaline inorganic salts such as trisodium phosphate, tricalcium phosphate, calcium sulfate and sodium or magnesium carbonate.

In an alkaline micro environment, preferably within a pH range of 7 to 11, trisodium phosphate, sodium carbonate and sodium lauryl sulfate have a stabilizing effect on the drug when the drug is in the tablet or capsule solid dosage form.

Suitable disintegrants for use in the present invention include corn starch, croscarmellose sodium and crospovidone.

Suitable glidents for use in the present invention include colloidal silicon dioxide and talc.

Magnesium and zinc stearate, sodium stearate fumarate and sodium and magnesium lauryl sulfate are among compatible lubricants that can be utilized in the preparations of the present invention.

In some formulations, the pH of the solid dosage form is very important to stability. The pH is preferably above 7, most preferably within the range of about 7–11. When the excipient is an inorganic salt, such as sodium carbonate, the pH is preferably within the range of about 8–11. When the excipient is sodium carbonate, the pH is most preferably about 10.8. When the excipient is maltodextrin, the pH is preferably about 7.0–7.6.

The moisture content of the solid dosage form, such as of a capsule or tablet, is also in some formulations important. It has been found that some solid dosage forms having a moisture content of 4.5% are unstable, whereas the same solid dosage forms with a moisture content of 3% were determined to be stable. Thus the moisture content is preferably less than 4.5% by weight, and for best stability of the product of the present invention a moisture limit of 0 to 3% by weight is more preferred.

A significant advantage of the preparations of the present invention is that the preparations can be prepared as a direct compression formula, dry granulation formula, or as a wet granulation formula, with or without preblending of the drug, although preferably with preblending, and still achieve remarkable stability of the resulting solid dosage form preparation.

It is particularly preferred that the filler or bulker in the stable solid dosage form preparations of the present invention be microcrystal line cellulose. It is also most preferred that the preparation be lactose-free. As indicated, it is preferred for the pH to be greater than 7 when the excipient is an inorganic salt. The pH in that case is preferably in the range of 7 to 11, and more preferably in the range of 8 to 11.

The amount of the thyroid hormone in the preparations of the present invention can vary widely, as desired. However, due to the high potency exhibited by most of the thyroid hormones, and especially levothyroxine sodium, normally very low amounts of the thyroid hormone will be utilized. The amounts will generally be less than 1% by weight, and normally less than 0.1% by weight. The minimum amount of the thyroid hormone can vary, so long as an effective amount is utilized to cause the desired pharmacological effect. In any event, the amount of the thyroid hormone that is conventionally used by the prior art in solid dosage form preparations may be utilized. Typically these prior art solid dosage form preparations will have a content of thyroid hormone of 25 micrograms to 300 micrograms.

Normally the excipient is a binder and/or a diluent and is preferably present in a predominate amount, preferably in the range of 50 to 99.99% by weight. More preferably the excipient will be present in an amount of from 65 to 95% by weight, more preferably from 80 to 92% by weight.

The disintegrants are normally used in a relatively low amount, preferably from 0 to 8% by weight. More preferably the amount is about 5% by weight.

The glident is normally used only when producing tablets, and generally will be within the range of 0 to 3% by weight. The lubricant will normally be in the range of 0 to 2% by weight, and preferably is about 0.5% by weight.

The solid dosage form preparations of the present invention can be prepared in a number of ways. Levothyroxine sodium or other thyroid hormone can be preblended with microcrystalline cellulose, maltodextrin and croscarmellose sodium. Magnesium stearate, sodium lauryl sulfate and colloidal silicon dioxide can then be added and blended for 5 minutes to obtain a final blend ready for compression or encapsulation. The dissolution rate of tablets or capsules can be manipulated by changing the concentration of croscarmellose sodium, or by changing the hardness of the tablet preparation.

In another process, levothyroxine or other thyroid hormones can be preblended with microcrystalline cellulose and then that blend can be blended with the rest of the microcrystalline cellulose, sodium carbonate and croscarmellose sodium. Magnesium stearate and colloidal silicon dioxide can be added with the mixture being blended for 5 minutes to obtain the final blend ready for compression or encapsulation. Such a composition typically has a pH, measured by dispensing a tablet in 10 ml of deionized water, of 9.5.

Alternatively, in the above composition the sodium carbonate can be eliminated, and a stable formula still obtained.

Alternatively, the sodium carbonate can be replaced by trisodium phosphate or sodium bicarbonate.

In yet another modification, the croscarmellose sodium can be replaced with starch.

The compositions of the present invention can also be prepared by blending the thyroid hormone with microcrystalline cellulose, maltodextrin and sodium lauryl sulfate. The resulting blend can be granulated with water and dried to a moisture content of around 3% or less. Such a preparation is stable to the extent that no potency loss is measured when stored at 40° C. and 75% relative humidity for 6 months (that is, the stability tested preparation retains at least 90% by weight of the initial weight (weight of the preparation after processing the preparation) of the thyroid hormone preparation). The granulation can be lubricated by the addition of magnesium stearate and subsequently tableted on a tablet press.

It should be noted that the wet granulations without binding agents could not be dried effectively using fluidized bed drying techniques, but can be dried using microwave energy or vacuum drying. On the other hand, granulations with a selected binding agent, such as hydroxypropyl cellulose, which forms granules, can be dried by fluidized bed drying. The above wet granulation formula can be modified by replacing the maltodextrin with trisodium phosphate or sodium carbonate, and mixing with the rest of the ingredients mentioned above. After granulation with water and drying to a moisture content of 3% or less, the dried granules can be lubricated with magnesium stearate and tableted using a tablet press. The stability data for such compositions show good stability of the finished product under accelerated conditions.

As mentioned, the fine particle size thyroid hormone, such as fine particle size levothyroxine sodium, results in rapid dissolution rates. It is preferred that at least 40% by weight of the tablet or other solid dosage form of thyroid hormone of the compositions of the present invention dissolve in water, and in pH 7.4 potassium phosphate buffer, in 80 minutes, using the procedure reported in tables 9–12. More preferably, at least 70% by weight, and more preferably at least 80% by weight of the solid dosage form thyroid hormone dissolves in 80 minutes in both buffer and water.

The dissolution rate of the drug from the tablets could be controlled by simply changing the concentration of the disintegrants, or by changing the hardness of the tablet. It has been found that better dissolution rates of the compositions of the present invention in dry blended formulations can be obtained if fine particle size levothyroxine sodium is utilized. It is preferred that the levothyroxine sodium or other thyroid hormone have a particle size of less than 40 microns, preferably less than 25 microns, and more preferably about 15 microns.

Preferably dissolution profiles of embodiments of the invention with small particle size and comprising maltodextrin are as follows:

| | |
|---|---|
| 20 minutes | 18 to 30% |
| 45 minutes | 40 to 60% |
| 80 minutes | 69 to 90% |

A further method of making the compositions of the present invention which is applicable to the use of fine particle size materials, and especially fine particle size thyroxine hormones, involves forming a preblend. A portion, suitably 10 to 15% by weight, of microcrystalline cellulose is mixed with the thyroid hormone, passed through a suitable screen, such as a 60 mesh screen, and mixed with sodium lauryl sulfate and blended until uniform, typically for about 20 minutes of blending, to form the preblend. The remaining ingredients except magnesium stearate are mixed together and passed through a suitable mesh screen, such as, for instance, an 18 mesh screen, and mixed with the preblend. The resulting mixture is blended until uniform, typically for about 2 hours or so. The magnesium stearate is added and then the resulting mix is blended until uniform, typically for about 5 minutes or so.

As mentioned, it is necessary to use vacuum or microwave drying for the wet granulation process, as otherwise unacceptable process loss is generally encountered. Since the thyroid hormones, and especially levothyroxine sodium, are thermally labile above 45° C., it is necessary to ensure that the drug has not been exposed to a temperature of greater than 45° C. for more than two hours.

The following examples are illustrative only and are not meant to limit the invention in any manner.

EXAMPLES OF THE INVENTION

Examples 1 to 16, 24 to 34 and 43 to 44 hereinbelow relate to dry, direct compression preparations, and Examples 17 to 23 and 35 to 42 relate to wet granulation preparations.

All proportions listed below are in percent by weight.

Example 1

An appropriate amount of levothyroxine sodium (suitably 0.02%), microcrystalline cellulose (suitably 90 to 100%), croscamiellose sodium (0 to 5%), magnesium stearate (0.5%), sodium lauryl sulfate (0 to 2%) and colloidal silicon dioxide (0 to 3%) may be utilized in this Example. The levothyroxine sodium and a proportion (16%) of the microcrystalline cellulose is preblended with conventional mixing equipment. The preblend and the remaining microcrystalline cellulose, together with the croscarmellose sodium, is mixed using conventional mixing equipment. Thereafter the magnesium stearate and colloidal silicon dioxide is added and blended for 5 minutes. A tableting machine is used to compress the resulting dry mixture into tablets.

Example 2

Example 1 is repeated, with the formulation based upon levothyroxine sodium (0.02%), microcrystalline cellulose (0 to 95%), croscarmellose sodium (0 to 5%), sodium lauryl sulfate (0 to 2%), maltodextrin (0 to 95%), magnesium stearate (0.5%) and colloidal silicon dioxide (0 to 3%).

Example 3

Example 1 is repeated, using levothyroxine sodium (0.02%), microcrystalline cellulose (80 to 95%), croscarmellose sodium (0 to 5%), sodium bicarbonate (0 to 15%), magnesium stearate (0.5%), and colloidal silicon dioxide (0 to 3%).

Example 4

Example 1 is repeated, using levothyroxine sodium (0.02%), microcrystalline cellulose (80 to 95%), croscarmellose sodium (0 to 5%), sodium carbonate (0 to 15%), magnesium stearate (0.5%), and colloidal silicon dioxide (0 to 3%).

Example 5

Example 1 is repeated, using levothyroxine sodium (0.02%), microcrystalline cellulose (80 to 100%), croscarmellose sodium (0 to 5%) colloidal silicon dioxide (0 to 3%), hydroxypropyl-β-cyclodextrin (0 to 0.2%) and magnesium stearate (0.5%).

Example 6

Example 1 is repeated, using levothyroxine sodium (0.02%), microcrystalline cellulose (80 to 95%), croscarmellose sodium (0 to 5%), trisodium phosphate (0 to 15%), magnesium stearate (0.5%), and colloidal silicon dioxide (0 to 3%).

Example 7

Example 1 is repeated, using levothyroxine sodium (0.02%), microcrystalline cellulose (50 to 100%), croscarmellose sodium (0 to 5%), mannitol (0 to 50%), magnesium stearate (0.5%), and colloidal silicon dioxide (0 to 3%).

Example 8

Example 1 is repeated, using levothyroxine sodium (0.02%), microcrystalline cellulose (40 to 100%), croscarmellose sodium (0 to 5%), tricalcium phosphate (0 to 50%), magnesium stearate (0.5%), and colloidal silicon dioxide (0 to 3%).

Example 9

Example 1 is repeated, using levothyroxine sodium (0.02%), microcrystalline cellulose (80 to 100%), croscarmellose sodium (0 to 5%), magnesium stearate (0.5%), and colloidal silicon dioxide (0 to 3%).

Example 10

Example 1 is repeated, using levothyroxine sodium (0.02%), microcrystalline cellulose (80 to 95%), croscarmellose sodium (0 to 5%), starch (0 to 15%), magnesium stearate (0.5%), and colloidal silicon dioxide (0 to 3%).

Example 11

Example 1 is repeated, using levothyroxine sodium (0.02%), microcrystalline cellulose (40 to 100%), croscarmellose sodium (0 to 5%), dicalcium phosphate (0 to 50%), magnesium stearate (0.5%), and colloidal silicon dioxide (0 to 3%).

Example 12

Example 1 is repeated, using levothyroxine sodium (0.02%), croscarmellose sodium (0 to 5%), microcrystalline cellulose (80 to 95%), hydroxypropyl cellulose (0 to 5%), magnesium stearate (0.5%), and colloidal silicon dioxide (0 to 3%).

Example 13

Example 1 is repeated, using levothyroxine sodium (0.02%), croscarmellose sodium (0 to 5%), microcrystalline cellulose (40 to 95%), galactose (0 to 50%), magnesium stearate (0.5%), and colloidal silicon dioxide (0 to 3%).

Example 14

Example 1 is repeated, using levothyroxine sodium (0.02%), glycine (0 to 95%), microcrystalline cellulose (0 to 95%), magnesium stearate (0.5%), croscarmellose sodium (0 to 5%) and colloidal silicon dioxide (0 to 3%).

Example 15

Example 1 is repeated, using levothyroxine sodium (0.02%), croscarmellose sodium (0 to 5%), microcrystalline cellulose (40 to 95%), calcium sulfate (0 to 50%), magnesium stearate (0.5%), and colloidal silicon dioxide (0 to 3%).

Example 16

Example 1 is repeated, using levothyroxine sodium (0.02%), croscarmellose sodium (0 to 5%), microcrystalline cellulose (80 to 9500%), magnesium carbonate (0 to 15%), magnesium stearate (0.5%), and sodium lauryl sulfate (0.2%).

The compositions of Examples 1 to 16 can also be incorporated into capsule dosage forms, instead of tablets.

Example 17

This Example uses levothyroxine sodium in a desired amount (0.02%), microcrystalline cellulose (0 to 85%), sodium lauryl sulfate (0 to 2%), trisodium phosphate (0 to 15%), croscarmellose sodium (0 to 5%), and magnesium stearate (0 to 0.5%). A preblend of levothyroxine sodium, a portion (16%) of the microcrystalline cellulose, and the sodium lauryl sulfate is prepared and placed in a mixing bowl. The rest of the microcrystalline cellulose and the croscarmellose sodium is added to the same bowl. The mixing is continued for several minutes and then the blend is granulated by the addition of a suitable amount of water (from 3.5 to 20% by weight). The water is evaporated off by microwave drying (vacuum drying could also be used). The granulation is sized and necessary and then blended with the magnesium stearate and colloidal silicon dioxide. The final blend is tableted on a tableting machine.

Example 18

Example 17 is repeated, but using a preparation based on levothyroxine sodium (0.02%), croscarmellose sodium (0 to 5%), microcrystalline cellulose (80 to 94%), sodium lauryl sulfate (0 to 2%), sodium carbonate (0 to 15%), magnesium stearate (0 to 0.5%), and colloidal silicon dioxide (0 to 3%).

Example 19

Example 17 is repeated, but using a preparation based on levothyroxine sodium (0.02%), croscarmellose sodium (0 to 5%), microcrystalline cellulose (85 to 100%), sodium lauryl sulfate (0 to 2%), colloidal silicon dioxide (0 to 3%), and magnesium stearate (0.5%).

Example 20

Example 17 is repeated, but using a preparation based on levothyroxine sodium (0.02%), croscarmellose sodium (0 to 5%), microcrystalline cellulose (50 to 100%), maltodextrin (Grade (M510) (50 to 100%), sodium lauryl sulfate (0 to 2%), colloidal silicon dioxide (0 to 3%), and magnesium stearate (0 to 0.5%).

Example 21

Example 17 is repeated, but using a preparation based on levothyroxine sodium (0.02%), croscarmellose sodium (0 to 5%), microcrystalline cellulose (50 to 94%), mannitol (0 to 50%), sodium lauryl sulfate (0 to 2%), colloidal silicon dioxide (0 to 3%), and magnesium stearate (0 to 0.5%).

Example 22

Example 17 is repeated, but using a preparation based on levothyroxine sodium (0.02%), croscarmellose sodium (0 to 5%), microcrystalline cellulose (0 to 95%), colloidal silicon dioxide (0 to 3%), magnesium stearate (0 to 0.5%) and sodium lauryl sulfate (0 to 2%).

Example 23

Example 17 is repeated, but using a preparation based on levothyroxine sodium (0.02%), croscarmellose sodium (0 to 5%), microcrystalline cellulose (0 to 50%), glycine (0 to 50%), magnesium stearate (0 to 0.5%) and sodium lauryl sulfate (0.2%).

Example 24–34

Direct compression preparations were prepared using the procedure of Example 1 with the compositions set forth in Table 1. The maltodextrin used was Grade M510.

TABLE 1

COMPOSITION OF DIRECT COMPRESSION FORMULAS

| INGREDIENTS | 24 | 25 | 26 | 27 | 28 | 29 | 30 | 31 | 32 | 33 | 34 |
|---|---|---|---|---|---|---|---|---|---|---|---|
| CROSCARMELOSE SODIUM | 6.500 | 6.500 | 6.500 | 6.500 | 6.500 | 6.500 | 6.500 | 6.500 | | 1.300 | 6.500 |
| COLLOIDAL SILICON DIOXIDE | 0.325 | | 0.325 | 3.900 | | 3.9 | 3.9 | | 0.332 | 0.325 | 0.325 |
| AVICEL ® PH 102* | 122.825 | | 57.84 | 103.322 | 39.000 | 103.322 | 103.322 | 122.795 | 65.78 | 63.04 | |
| AVICEL ® PH 112* | | | | | | | | | | | 122.825 |
| GLYCINE | | | | | 83.822 | | | | | | |
| LEVOTHYROXINE SODIUM | 0.025 | 0.025 | 0.025 | 0.025 | 0.025 | 0.025 | 0.025 | 0.025 | 0.025 | 0.025 | 0.025 |
| MAGNESIUM STEARATE, NF | 0.650 | 0.650 | 0.650 | 0.650 | 0.650 | 0.650 | 0.650 | 0.650 | 0.664 | 0.650 | 0.650 |
| MALTODEXTRIN | | 122.825 | 64.99 | | | | | | 66.43 | 65.0 | |
| HYDROXYPROPYL-β CYCLODEXTRIN | | | | | | | | 0.028 | | | |
| TRISODIUM PHOSPHATE | | | | 19.500 | | | | | | | |
| SODIUM BICARBONATE | | | | | | 19.500 | | | | | |
| SODIUM CARBONATE | | | | | | | 19.500 | | | | |
| SODIUM LAURYL SULFATE | | | | | | | | | 0.664 | 0.650 | |
| TOTAL (mg per unit) | 130.33 | 130.00 | 130.33 | 133.90 | 130.00 | 133.90 | 133.90 | 130.00 | 133.90 | 130.99 | 130.33 |

*BRAND OF MICROCRYSTALLINE CELLULOSE

Certain of the tablets of Examples 24 to 34 were subjected to stability testing. The same criteria that was used for the dry compression tablets was used in selecting tablets for stability testing. Tablets selected for stability testing were those that had good content uniformity (e.g., less 10% process loss or a relative standard deviation less than 10%), good tableting characteristics (e.g., good flow characteristics, an angle of repose greater then 42°, and good tableting). Each tablet selected for stabilt testing, having a weight of approximately 130 mg, was subjected to testing in the presence and absence of a desiccant at 30° C. (See Table 2), at 40° C. (See Table 3), and at 40° C. and 75% relative humidity (See Table 4).

TABLE 2

STABILITY OF DIRECT COMPRESSION FORMULAS
30° C. With and Without Desiccant

| | | With Desiccant | | | | Without Desiccant | | |
|---|---|---|---|---|---|---|---|---|
| Example | Initial | 1 Month | 2 Months | 3 Months | 6.5 Months | 1 Month | 2 Months | 3 Months | 6.5 Months |
| Example 30 | 97.3 | 97.1 (−0.2) | 97.9, 95.3 96.6 (−0.6) | 97.1 (−0.2) | 97.7 (0.4) | 97.8 (+2.5) | 97.1, 96.7 96.9 (−1.4) | 96.3 (−1) | 96.7 (−0.6) |
| Example 24 | 96.7 | 100.1 (+3.4) | 95.3, 92.3 93.8 (−2.9) | 95.9 (−0.8) | | 98.7 (+2) | 95.9, 95.9 95.9 (−0.8) | 95.2 (−1.5) | |
| Example 34 | 99.8 | 101.9 (+2.0) | 101.0, 96.8 98.9 (−0.9) | 95.9 (−3.9) | | 99.7 (−0.1) | 103.7, 102.6 103.2 (−0.1) | 98.9 (−0.9) | |
| Example 29 | 99.9 | 98.8 (−1.1) | 100.2, 98.2 99.2 (−0.7) | 98.6 (−1.3) | | 101.1 (+1.2) | 99.8, 96.6 98.2 (−1.7) | 98.0 (−1.9) | |

TABLE 3

STABILITY OF DIRECT COMPRESSION FORMULAS
Stability of Levothyroxine Sodium Tablets at 40° C.
With and Without Desiccant

| | | With Desiccant | | | Without Desiccant | | |
|---|---|---|---|---|---|---|---|
| Example | Initial | 1 Month | 2 Months | 3 Months | 1 Month | 2 Months | 3 Months |
| Example 29 | 99.9 | 101.5 (−1.6) | 97.0 (−2.9) | 95.5 (−4.4) | 101.2 (+1.3) | 97.0 (+2.9) | 97.5 (−2.4) |
| Example 24 | 96.7 | 98.1 (+1.6) | 96.2 (−0.5) | 95.0 (−1.0) | 96.5 (0.2) | 93.8 (−2.9) | 96.4 (−0.3) |
| Example 34 | 99.8 | 98.5 (−1.3) | 97.5 (−2.3) | 93.1 (−6.7) | 97.7 (−2.1) | 97.4 (−2.4) | 92.7 (−7.1) |
| Example 30 | 97.3 | 101.2 (+3.9) | 95.1 (−2.2) | 95.0 (−2.3) | 100.6 (+3.3) | 92.4 (−4.9) | 94.6 (−2.7) |

TABLE 4

STABILITY OF DIRECT COMPRESSION FORMULAS
40° C./75% RH with Desiccant

| Example | Initial | 1 Month | 2 Months | 3 Months | 6.5 Months |
|---|---|---|---|---|---|
| Example 30 | 97.3 | 101.0 | 97.9, 95.3 96.6 (−0.7) | 97.0 (−0.3) | 92.4 (−4.9) |
| Example 24 | 96.7 | 99.1 | 95.4, 93.4 94.4 (−2.3) | 95.8 (−0.9) | |
| Example 34 | 99.8 | 96.5 | 97.4, 94.9 | 91.2 | |
| Example 29 | 99.9 | 105.2 | 98.5, 96.0 97.3 (−2.6) | 96.2 (−3.6) (−5.3) 95.6 (−4.3) | |

The amount of levothyroxine sodium in the initial tablets and in the tested tablets were measured and are reported in Tables 2–4. The percentages in Tables 2–4 represent the actual percentage of the tablets as measured against a standard and do not represent the percent of the initial value. The numbers in the parenthesis of Table 1 represent the percent difference of the average value of the tablets when compared to the initial value measured. It will be noted that at 3 months accelerated aging all samples had more than 90% of the original levothyroxine sodium present, and the preferred samples had more than 95% of the original levothyroxine present still remaining.

Examples 24–26 had less than 90% of the initial concentration and the pH of these samples was about 6. Example 27, made with tris odium phosphate also had less than 90% of the initial concentration but the example had a moisture content of about 4.5%. No assay was available for accurate testing of Example 28. Examples 29, 39 and 33 all had values of greater than 90% of the initial concentration. Examples 31 and 32 had values of about 88% of the initial concentration.

Examples 35 to 42

Example 17 is repeated, but using the compositions set forth in Table 5.

TABLE 5

COMPOSITION OF WET GRANULATION FORMULAS

| Ingredient | Example 35 | Example 36 | Example 37 | Example 38 | Example 39 | Example 40 | Example 41 | Example 42 |
|---|---|---|---|---|---|---|---|---|
| CROSCARMELLOSE SODIUM | 2.62 | 2.6 | 6.500 | 6.500 | 6.500 | 6.500 | 9.03 | 6.500 |
| COLLOIDAL SILICON DIOXIDE | 0.325 | 0.325 | 0.325 | 3.9 | 0.325 | 0.325 | 0.44 | 0.325 |
| AVICEL ® PH 102* | 57.77 | 64.995 | 106.860 | 19.5 | | | 122.85 | 80.33 | 106.86 |
| AVICEL ® PH 112* | | | | | 122.83 | | | |
| GLYCINE | | | | | 103.332 | | | |
| LEVOTHYROXINE SODIUM | 0.025 | 0.025 | 0.025 | 0.025 | 0.025 | 0.025 | 0.025 | 0.025 |
| MAGNESIUM STEARATE, NF | 0.650 | 0.650 | 0.650 | 0.650 | 0.650 | 0.650 | 0.650 | 0.650 |
| MALTODEXTRIN | 65.0 | 64.995 | | | | | 84.36 | |
| PURIFIED WATER, USP (DEIONIZED) | **4.360 | **4.380 | **26.2 | **0.005 | **26.2 | **26.2 | **8.7 | **26.2 |
| SODIUM LAURYL SULFATE | 0.650 | | 0.650 | | 0.650 | 0.650 | 0.620 | 0.65 |
| TRISODIUM PHOSPHATE | | | | | | | | 15.98 |
| SODIUM CARBONATE | | | | 15.98 | | | | |
| HYDROXYPROPYL CELLULOSE | 3.93 | | | | | | | |
| TOTAL (mg per unit) | 130.97 | 133.59 | 130.99 | 133.91 | 130.98 | 175.46 | 175.46 | 130.99 |

*Brand of Microcrystalline Cellulose
**Removed During Drying Process

Certain of the tablets of Examples 37 to 42 (35 and 36 were not tested for stability) and were subjected to stability testing, and the results are reported in Tables 6, 7, and 8. The criteria for selecting samples for stability testing was essentially the same as the criteria used for testing of It will be noted that all of the compositions, except Example 42 at 40° C. with desiccant, had at least 90% by weight of the original levothyroxine sodium remaining, and the preferred compositions had at least 95% of the levothyroxine remaining.

TABLE 6

STABILITY OF WET GRANULATION FORMULAS
Stability of Levothyroxine Sodium Tablets at 30° C. With and Without Desiccant

| | | With Desiccant | | | | Without Desiccant | | |
|---|---|---|---|---|---|---|---|---|
| Example | Initial | 1 Month | 2 Months | 3 Months | 4 Months | 1 Month | 2 Months | 3 Months | 4 Months |
| Example 37 | 106.4 | 100.5 | 107.3 | 102.6 | | 102.7 | 106.3 | 105.8 | |
| Example 42 | 99.4 | 93.3 | 100.5 | 99.5 | | 93.5 | 98.6 | 93.8 | |
| Example 39 | 108.0 | 105.7 | 103.7 | 104.6 | | 107.4 | 103.7 | 107.3 | |
| Example 41 | 101.0 | 104.4 | 100.7 | 100.9 | 103.0 | 103.3 | 102.7 | 103.2 | 103.4 |

TABLE 7

STABILITY OF WET GRANULATION FORMULAS
Stability of Levothyroxine Sodium Tablets at 40° C.
With and Without Desiccant

| | | With Desiccant | | | Without Desiccant | | |
|---|---|---|---|---|---|---|---|
| Example | Initial | 1 Month | 2 Months | 3 Months | 1 Month | 2 Months | 3 Months |
| Example 37 | 106.4 | 100.2 | 104.3 | 103.1 | 98.2 | 101.9 | 101.3 |
| Example 42 | 99.4 | 94.3 | 97.7 | 95.8 | 93.9 | 92.3 | 92.4 |
| Example 39 | 108.0 | 105.6 | 103.0 | 108.0 | 102.4 | 98.8 | 105.8 |

TABLE 7-continued

STABILITY OF WET GRANULATION FORMULAS
Stability of Levothyroxine Sodium Tablets at 40° C.
With and Without Desiccant

| Example | Initial | With Desiccant | | | Without Desiccant | | |
|---|---|---|---|---|---|---|---|
| | | 1 Month | 2 Months | 3 Months | 1 Month | 2 Months | 3 Months |
| Example 41 | 101.8 | 103.4 | 99.8 | 102.6 | 103.2 | 101.7 | 102.5 |

TABLE 8

STABILITY OF WET GRANULATION FORMULAS
Stability Levothyroxine Sodium Tablets at 40° C./75% RH With and Without Desiccant

| Example | Initial | With Desiccant | | | | Without Desiccant | | | |
|---|---|---|---|---|---|---|---|---|---|
| | | 1 Month | 2 Months | 3 Months | 4 Months | 1 Month | 2 Months | 3 Months | 4 Months |
| Example 37 | 106.4 | 100.0 | 100.0 | 101.3 | | 97.3 | 101.9 | 99.5 | |
| Example 42 | 99.4 | 89.3 | 94.5 | 88.9 | | 94.1 | 98.3 | 92.0 | |
| Example 39 | 108.0 | 103.8 | 89.2 | 107.1 | | 103.3 | 87.9 | 104.8 | |
| Example 41 | 101.8 | 104.4 | 102.7 | 101.2 | 99.9 | 104.4 | 102.8 | 102.5 | 101.4 |

Dissolution Profiles

A number of tablets produced by dry compression in Examples 24 to 34 and by wet granulation in Examples 35 to 42 were tested for dissolution profiles. The actual 5 tablets tested represent tablets not placed on stability ("initial") and were not more than about 5 days old. A tablet was placed in a vessel containing 50 ml of distilled water or buffer and maintained at 37° C. stirred by a paddle revolving at 100 RPM. The percent of the levothyroxine sodium which dissolved in the water or, as indicated, buffer solution was measured and is reported in Tables 9, 10, 11 and 12.

TABLE 9

DIRECT COMPRESSION FORMULAS -
DISSOLUTION IN PH 7.4 POTASSIUM
PHOSPHATE BUFFER (INITIAL)

| Example | 20 Minutes | 45 Minutes | 80 Minutes |
|---|---|---|---|
| Example 24 | — | 39.0 | 43.6 |
| Example 34 | — | 45.4 | 49.9 |
| Example 30 | 48.9 | 53.7 | 56.6 |
| Example 26 | 56.6 | 63.2 | 64.5 |
| Example 27 | 64.5 | 73.3 | 73.5 |
| Example 25 | 35.5 | 56.4 | 57.3 |
| Example 29 | 25.8 | 31.3 | 36.2 |
| Example 32 | 29.2 | 76.5 | 85.5 |

TABLE 10

DIRECT COMPRESSION FORMULAS -
DISSOLUTION PROFILES IN WATER
(INITIAL)

| Example | 20 Minutes | 45 Minutes | 80 Minutes |
|---|---|---|---|
| Example 24 | 65.8 | 72.9 | 68.1 |
| Example 34 | 73.3 | 82.1 | 79.5 |
| Example 30 | 104.8 | 105.5 | 105.6 |
| Example 29 | 76.3 | 78.4 | 84.8 |
| Example 27 | 94.8 | 100.3 | 97.1 |
| Example 26 | 83.6 | 85.6 | 87.7 |
| Example 25 | 33.6 | 53.1 | 54.8 |
| Example 32 | 28.3 | 59.4 | 68.7 |

TABLE 11

WET GRANULATION FORMULA -
DISSOLUTION PROFILES IN PH
7.4 POTASSIUM PHOSPHATE BUFFER (INITIAL)

| Example | 20 Minutes | 45 Minutes | 80 Minutes |
|---|---|---|---|
| Example 39 | 47.6 | 47.9 | 54.0 |
| Example 41 | 76.0 | 90.2 | 83.3 |
| Example 37 | 73.7 | 78.2 | 90.1 |
| Example 42 | 76.8 | 87.3 | 105.2 |
| Example 36 | 48.129.2 | 72.1 | 79.9 |

TABLE 12

WET GRANULATION FORMULA -
DISSOLUTION PROFILES IN WATER (INITIAL)

| Example | 20 Minutes | 45 Minutes | 80 Minutes |
|---|---|---|---|
| Example 39 | 80.0 | 90.1 | 93.1 |
| Example 41 | 85.0 | 89.4 | 92.0 |
| Example 37 | 110.7 | 110.8 | 109.5 |
| Example 42 | 110.5 | 111.9 | 111.9 |
| Example 36 | 15.9 | 43.3 | 55.7 |

Example 43

This example was based on the following components (110 mg tablets):

| | |
|---|---|
| Maltodextrin: | 54.3 mg (49.4%) |
| AVICEL ® PH 102: | 54.3 mg (49.4%) |

-continued

| | |
|---|---|
| Sodium lauryl sulfate: | 0.55 mg (0.5%) |
| Magnesium stearate: | 0.55 mg (0.5%) |
| Colloidal silicon dioxide: | 0.0275 mg (0.02%) |
| Levothyroxine sodium: | 0.025, 0.100 and 0.300 mg (0.02–0.3%) |

Approximately 13% of the AVICEL® was mixed with the levothyroxine sodium (15 micron particle size), passed through a 60 mesh screen, and then mixed with the sodium lauryl sulfate and blended for about 20 minutes to form a preblend. The maltodextrin, the rest of the AVICEL® PH 102, and the colloidal silicon dioxide were mixed together and then passed through an 18 mesh screen. The product passing through the screen was mixed with the preblend formed above, and blended for approximately 2 hours until a uniform mixture was obtained. The magnesium stearate was then added, and the resulting mixture blended for approximately 5 minutes until uniform. The dry formulation was compressed on a tableting machine into tablets, each of approximately 110 mg in weight, having a pH of about 7.4 when dissolved in water of 7.4 (one table per five milliliters of water). The tablets produced in this Example had the same dissolution profile in both water and pH 7.4 potassium phosphate buffer when tested according to the dissolution profile test described above.

TABLE 13

(25 μg)

| Condition | Interval | Potency (%) | % of Initial | | Dissolution Profile (%) | | |
|---|---|---|---|---|---|---|---|
| | | | | | 20 min | 45 min | 80 min |
| Initial | Initial | 95.7 | | water | 33.0 | 67.0 | 69.0 |
| | | | | buffer | 26.0 | 54.0 | 73.0 |
| 40 C./75% RH w/desc | 1 Month | 92.3 | 96.4 | b | 21.0 | 48.0 | 70.0 |
| | 2 Month | 91.6 | 95.7 | b | 13.0 | 61.0 | 74.0 |
| | 3 Month | 90.8 | 94.9 | b | 26.0 | 55.0 | 69.0 |
| | | | | w | 24.0 | 53.0 | 63.0 |
| | 6 Month | 90.2 | 94.3 | b | 24.0 | 51.0 | 66.0 |
| | | | | w | 25.0 | 57.0 | 60.0 |
| 30 C./60% RH w/desc | 1 Month | 94.9 | 99.2 | b | 21.0 | 54.0 | 70.0 |
| | 2 Month | 94.5 | 98.7 | b | 24.0 | 50.0 | 71.0 |
| | 3 Month | 94.7 | 99.0 | b | 12.0 | 60.0 | 78.0 |
| | | | | w | 19.0 | 61.0 | 63.0 |
| | 6 Month | 95.1 | 99.4 | b | 34.0 | 53.0 | 70.0 |
| | | | | w | 17.0 | 44.0 | 68.0 |
| 25 C./60% RH w/desc | 1 Month | 96.5 | 100.8 | b | 25.0 | 64.0 | 75.0 |
| | 2 Month | 93.7 | 97.9 | b | 25.0 | 55.0 | 71.0 |
| | 3 Month | 96.8 | 101.1 | b | 33.0 | 64.0 | 78.0 |
| | | | | w | 20.0 | 51.0 | 62.0 |
| | 6 Month | 96.2 | 100.5 | b | 28.0 | 65.0 | 77.0 |
| | | | | w | 28.0 | 51.0 | 62.0 |

TABLE 14

(100 μg)

| Condition | Interval | Potency (%) | % of Initial | | Dissolution Profile (%) | | |
|---|---|---|---|---|---|---|---|
| | | | | | 20 min | 45 min | 80 min |
| INITIAL | Initial | 96.8 | | water | 27.0 | 59.0 | 67.0 |
| | | | | buffer | 27.0 | 63.0 | 74.0 |
| 40 C./75% RH w/desc | 1 Month | 95.6 | 98.8 | b | 24.0 | 65.0 | 73.0 |
| | 2 Month | 94.0 | 97.1 | b | 26.0 | 61.0 | 76.0 |
| | 3 Month | 92.8 | 95.9 | b | 26.0 | 59.0 | 74.0 |
| | | | | w | 20.0 | 50.0 | 66.0 |
| | 6 Month | 91.9 | 94.9 | b | 24.0 | 49.0 | 67.0 |
| | | | | w | 16.0 | 43.0 | 55.0 |
| 30 C./60% RH w/desc | 1 Month | 96.1 | 99.3 | b | 23.0 | 51.0 | 72.0 |
| | 2 Month | 95.7 | 98.9 | b | 24.0 | 53.0 | 75.0 |
| | 3 Month | 96.8 | 100.0 | b | 25.0 | 57.0 | 76.0 |
| | | | | w | 23.0 | 60.0 | 65.0 |
| | 6 Month | 94.8 | 97.9 | b | 23.0 | 46.0 | 67.0 |
| | | | | w | 18.0 | 50.0 | 61.0 |
| 25 C./60% RH w/desc | 1 Month | 97.2 | 100.4 | b | 24.0 | 57.0 | 74.0 |
| | 2 Month | 97.2 | 100.4 | b | 31.0 | 51.0 | 74.0 |
| | 3 Month | 96.6 | 99.8 | b | 25.0 | 64.0 | 73.0 |
| | | | | w | 22.0 | 54.0 | 62.0 |
| | 6 Month | 97 | 100.2 | b | 22.0 | 44.0 | 65.0 |
| | | | | w | 22.0 | 51.0 | 60.0 |

TABLE 15

(300 μg)

| Condition | Interval | Potency (%) | % of Initial | | Dissolution Profile (%) | | |
|---|---|---|---|---|---|---|---|
| | | | | | 20 min | 45 min | 80 min |
| INITIAL | Initial | 98.7 | | water | 26.0 | 63.0 | 70.0 |
| | | | | buffer | 24.0 | 60.0 | 71.0 |
| 40 C./75% RH w/desc | 1 Month | 97.7 | 99.0 | b | 18.0 | 50.0 | 69.0 |
| | 2 Month | 96.7 | 98.0 | b | 19.0 | 46.0 | 68.0 |
| | 3 Month | 93.5 | 94.7 | b | 28.0 | 63.0 | 71.0 |
| | | | | w | 18.0 | 47.0 | 59.0 |
| | 6 Month | 94.2 | 95.4 | b | 19.0 | 43.0 | 68.0 |
| | | | | w | 22.0 | 50.0 | 64.0 |
| 30 C./60% RH w/desc | 1 Month | 99.1 | 100.4 | b | 33.0 | 65.0 | 76.0 |
| | 2 Month | 97.2 | 98.5 | b | 24.0 | 58.0 | 73.0 |
| | 3 Month | 98.4 | 99.7 | b | 17.0 | 45.0 | 67.0 |
| | | | | w | 14.0 | 46.0 | 58.0 |
| | 6 Month | 101 | 102.3 | b | 18.0 | 42.0 | 68.0 |
| | | | | w | 22.0 | 54.0 | 65.0 |
| 25 C./60% RH w/desc | 1 Month | 98.2 | 99.5 | b | 21.0 | 46.0 | 76.0 |
| | 2 Month | 98.4 | 99.7 | b | 23.0 | 63.0 | 74.0 |
| | 3 Month | 99.3 | 100.6 | b | 22.0 | 53.0 | 68.0 |
| | | | | w | 17.0 | 53.0 | 67.0 |
| | 6 Month | 100.3 | 101.6 | b | 21.0 | 55.0 | 73.0 |
| | | | | w | 22.0 | 57.0 | 64.0 |

The Tablets of this Example (for all strengths) tested at 40° C. and 75% RH for three and six months had a potency loss of less than or equal to about 5% of the initial measurement.

Example 44

Example 43 was repeated, but using the following components:

Levothyroxine sodium (15 micron particle size): 0.025, 100, and 300 mg (0.02%–0.2%)

| | |
|---|---|
| AVICEL ® PH 102: | 86.6 mg (78%) |
| Sodium carbonate: | 16.5 mg (15.%) |
| Magnesium stearate: | 0.55 mg (0.5%) |
| Sodium lauryl sulfate: | 0.55 mg (0.5%) |
| Colloidal silicon dioxide: | 0.0275 mg (0.025%) |
| Croscarmellose sodium: | 5.5 mg (5%) |

A preblend was formed by mixing together approximately 13% of the AVICEL and the levothyroxine sodium, and passing the mixture through a 60 mesh screen. The mixture was then mixed with the sodium lauryl sulfate and blended for about 20 minutes to form the preblend. The croscarmellose sodium, the remainder of the AVICEL, the sodium carbonate and the colloidal silicon dioxide were mixed together and the mixture was passed through an 18 mesh screen. The product passing through the screen was mixed with the preblend formed above, and blended for approximately 2 hours until a uniform mixture was obtained. The magnesium stearate was then added, and the resulting mixture blended for approximately 5 minutes until uniform. The dry formulation was compressed on a tableting machine into tablets, each of approximately 110 mg in weight, having a pH when dissolved in water of 10.8.

TABLE 16

(25 µg)

| Condition | Interval | Potency (%) | % of Initial | | Dissolution Profile (%) | | |
|---|---|---|---|---|---|---|---|
| | | | | | 20 min | 45 min | 80 min |
| INITIAL | Initial | 99.9 | | wafer | 91.0 | 95.0 | 96.0 |
| | | | | water | 104.0 | 102.0 | 100.0 |
| 40 C./75% RH w/desc | 1 Month | 94.7 | 94.8 | b | 96.0 | 97.0 | 98.0 |
| | 2 Month | 92.6 | 92.7 | b | 90.0 | 93.0 | 93.0 |
| | 3 Month | 90.8 | 90.9 | b | 84.0 | 84.0 | 85.0 |
| | | | | w | 92.0 | 92.0 | 93.0 |
| | 6 Month | 87.6 | 87.7 | | | | |
| 30 C./60% RH w/desc | 1 Month | 98.8 | 98.9 | b | 94.0 | 94.0 | 94.0 |
| | 2 Month | 99.6 | 99.7 | b | 96.0 | 88.0 | 91.0 |
| | 3 Month | 96.6 | 96.7 | b | 89.0 | 90.0 | 91.0 |
| | | | | w | 100.0 | 100.0 | 98.0 |
| | 6 Month | 94.9 | 95.0 | | | | |
| 25 C./60% RH w/desc | 1 Month | 98.6 | 98.7 | b | 97.0 | 98.0 | 98.0 |
| | 2 Month | 98.9 | 99.0 | b | 91.0 | 93.0 | 92.0 |
| | 3 Month | 97.6 | 97.7 | b | 95.0 | 96.0 | 94.0 |
| | | | | w | 101.0 | 101.0 | 101.0 |
| | 6 Month | 96.9 | 97.0 | | | | |

TABLE 17

(100 µg)

| Condition | Interval | Potency (%) | % of Initial | | Dissolution Profile (%) | | |
|---|---|---|---|---|---|---|---|
| | | | | | 20 min | 45 min | 80 min |
| INITIAL | Initial | 100.0 | | buffer | 92.0 | 92.0 | 95.0 |
| | | | | water | 89.0 | 99.0 | 99.0 |
| 40 C./75% RH w/desc | 1 Month | 94.8 | 94.8 | b | 95.0 | 98.0 | 98.0 |
| | 2 Month | 93.5 | 93.5 | b | 89.0 | 91.0 | 91.0 |
| | 3 Month | 92.4 | 92.4 | b | 85.0 | 86.0 | 88.0 |
| | | | | w | 90.0 | 90.0 | 90.0 |
| | 6 Month | 86.9 | 86.9 | | | | |
| 30 C./60% RH w/desc | 1 Month | 97.4 | 97.4 | b | 90.0 | 92.0 | 91.0 |
| | 2 Month | 98.0 | 98.0 | b | 93.0 | 96.0 | 95.0 |
| | 3 Month | 99.1 | 99.1 | b | 92.0 | 93.0 | 93.0 |
| | | | | w | 97.0 | 99.0 | 98.0 |
| | 6 Month | 95.7 | 95.7 | | | | |
| 25 C./60% RH w/desc | 1 Month | 99.9 | 99.9 | b | 92.0 | 91.0 | 91.0 |
| | 2 Month | 98.4 | 98.4 | b | 96.0 | 96.0 | 98.0 |
| | 3 Month | 98.5 | 98.5 | b | 97.0 | 98.0 | 99.0 |
| | | | | w | 98.0 | 100.0 | 98.0 |
| | 6 Month | 97.7 | 97.7 | | | | |

TABLE 18

(300 µg)

| Condition | Interval | Potency (%) | % of Initial | | Dissolution Profile (%) | | |
|---|---|---|---|---|---|---|---|
| | | | | | 20 min | 45 min | 80 min |
| INITIAL | Initial | 98.9 | | buffer | 91.0 | 93.0 | 91.0 |
| | | | | water | 99.0 | 98.0 | 99.0 |
| 40 C./75% RH w/desc | 1 Month | 93.2 | 94.2 | b | 89.0 | 90.0 | 91.0 |
| | 2 Month | 90.2 | 91.2 | b | 88.0 | 89.0 | 89.0 |
| | 3 Month | 88.9 | 89.9 | b | 85.0 | 87.0 | 86.0 |
| | | | | w | 88.0 | 89.0 | 89.0 |
| | 6 Month | 85.2 | 86.1 | | | | |
| 30 C./60% RH w/desc | 1 Month | 97.3 | 98.4 | b | 91.0 | 92.0 | 94.0 |
| | 2 Month | 96.0 | 97.1 | b | 90.0 | 92.0 | 95.0 |
| | 3 Month | 94.8 | 95.9 | b | 89.0 | 89.0 | 90.0 |
| | | | | w | 97.0 | 97.0 | 98.0 |
| | 6 Month | 93.3 | 94.3 | | | | |
| 25 C./60% RH w/desc | 1 Month | 98.5 | 99.6 | b | 92.0 | 94.0 | 94.0 |
| | 2 Month | 97.6 | 98.7 | b | 94.0 | 96.0 | 97.0 |
| | 3 Month | 96.8 | 97.9 | b | 88.0 | 89.0 | 90.0 |
| | | | | w | 96.0 | 99.0 | 98.0 |
| | 6 Month | 100.4 | 101.5 | | | | |

The tablets of this Example 44 had particularly rapid dissolution profiles. In both water and pH 7.4 potassium phosphate buffer more than 70% of the levothyroxine sodium was dissolved in 20 minutes in the dissolution profile test described above. The invention has been described with reference to various specific embodiments. However, many variations and modifications may be made while remaining within the scope and spirit of the invention.

We claim:

1. A stable, solid dosage form pharmaceutical preparation suitable for the treatment of thyroid disorders, said preparation comprising:
   an effective amount of a thryoxine drug; and a water soluble glucose polymer;
   said preparation being stable to the extent that substantially no potency loss is measured when the preparation is stored at 40° C. and 75% relative humidity for 3 months.

2. The preparation of claim 1, wherein the preparation is in a unit dose form.

3. The preparation of claim 2, wherein the unit dose form is a tablet.

4. The preparation of claim 3, wherein the tablet additionally includes a lubricant and a binder.

5. The preparation of claim 4, wherein the tablet also contains a glidant.

6. The preparation of claim 2, wherein the unit dose form is a capsule.

7. The preparation of claim 1, wherein the capsule also contain a lubricant and a glidant.

8. The preparation of claim 1, wherein the preparation is in the form of a powder.

9. The preparation of claim 1, wherein the polymer is selected from the group consisting of maltodextrin, β-cyclodextrin and hydroxypropyl-β-cyclodextrin.

10. The preparation of claim 1 wherein the pH of the preparation is about 7 to 11.

11. The preparation of claim 1 wherein the thyroxine drug is levothyroxine sodium.

12. The preparation of claim 1 wherein the preparation contains less than 5% by weight of the total of lactose, glucose and sucrose.

13. The preparation of claim 12 wherein the preparation contains substantially no lactose, glucose or sucrose.

14. Preparation of claim 1, wherein the preparation, when stored at 40° C. and 75% RH for 3 months, exhibits less than 10% by weight loss of the thyroxine drug.

15. A stable pharmaceutical composition comprising:
   a. an effective amount of a thyroxine drug;
   b. a water soluble polysaccharide; and
   c. a free water content less than 4.5% by weight of the preparation, wherein the pH of the composition has a pH greater than about 7.

16. The composition of claim 15 wherein the water-soluble polysaccharide is polysaccharide having a dextrose value of less than 25.

17. The composition of claim 15 wherein the water soluble polysaccharide is a polysaccharide having a dextrose value of less than 10.

18. The composition of claim 15 wherein the water soluble polysaccharide comprises a polysaccharide selected from group consisting of maltodextrin, β cyclodextrin, and hydroxypropyl-β-cyclodextrin.

19. The composition of claim 15, wherein the preparation is a unit dose form.

20. The composition of claim 16, wherein the preparation is a unit dose form.

21. The composition of claim 17, wherein the preparation is a unit dose form.

22. The composition of claim 18, wherein the preparation is a unit dose form.

23. The composition of claim 19, wherein the unit dose form is a tablet.

24. The composition of claim 20, wherein the unit dose form is a tablet.

25. The composition of claim 21, wherein the unit dose form is a tablet.

26. The composition of claim 22, wherein the unit dose form is a tablet.

27. The composition of claim 23, wherein the tablet additionally includes a lubricant and a binder.

28. The composition of claim 24, wherein the tablet additionally includes a lubricant and a binder.

29. The composition of claim 25, wherein the tablet additionally includes a lubricant and a binder.

30. The composition of claim 26, wherein the tablet additionally includes a lubricant and a binder.

31. The preparation of claim 23, wherein the tablet also contains a glidant.

32. The preparation of claim 24, wherein the tablet also contains a glidant.

33. The preparation of claim 25, wherein the tablet also contains a glidant.

34. The preparation of claim 26, wherein the tablet also contains a glidant.

35. The preparation of claim 27, wherein the tablet also contains a glidant.

36. The preparation of claim 28, wherein the tablet also contains a glidant.

37. The preparation of claim 29, wherein the tablet also contains a glidant.

38. The preparation of claim 30, wherein the tablet also contains a glidant.

* * * * *